United States Patent [19]
Geigle et al.

[11] Patent Number: 5,372,989
[45] Date of Patent: Dec. 13, 1994

[54] WATER-DISPERSIBLE OR WATER-SOLUBLE PESTICIDE GRANDULES FROM HEAT-ACTIVATED BINDERS

[75] Inventors: William L. Geigle, Downs, Ill.; Lionel S. Sandell, Wilmington; Robert D. Wysong, Talleyville, both of Del.

[73] Assignee: E. I. Du Pont de Nemours and Company, Wilmington, Del.

[21] Appl. No.: 934,467

[22] PCT Filed: Feb. 27, 1991

[86] PCT No.: PCT/US91/01105
§ 371 Date: Sep. 11, 1992
§ 102(e) Date: Sep. 11, 1992

[87] PCT Pub. No.: WO91/13546
PCT Pub. Date: Sep. 19, 1991

[51] Int. Cl.⁵ .................. A01N 25/08; A01N 25/30; A01N 25/12
[52] U.S. Cl. .................. 504/116; 504/212; 504/323; 504/268; 71/DIG. 1; 424/409
[58] Field of Search .................. 504/116; 71/DIG. 1; 424/409

[56] References Cited

U.S. PATENT DOCUMENTS

| | | | |
|---|---|---|---|
| 4,310,483 | 1/1982 | Dörfel et al. | 264/117 |
| 4,558,040 | 12/1985 | Pilgram et al. | 514/150 |
| 4,604,100 | 8/1986 | Schneider et al. | 8/526 |
| 4,686,209 | 8/1987 | Fahmy | 514/116 |
| 4,707,287 | 11/1987 | Herdeman | 252/91 |
| 4,767,557 | 8/1988 | Herdeman | 252/91 |
| 4,867,972 | 9/1989 | Girardeau et al. | 424/409 |
| 4,931,080 | 6/1990 | Chan et al. | 71/DIG. 1 |
| 4,936,901 | 6/1990 | Surgant, Sr. et al. | 71/92 |

FOREIGN PATENT DOCUMENTS

| | | |
|---|---|---|
| 0206537 | 12/1986 | European Pat. Off. |
| 0256608 | 2/1988 | European Pat. Off. |
| 2645709 | 10/1990 | France |
| 2143519 | 3/1973 | Germany |
| 52/30577 | 8/1977 | Japan |
| 59-156422 | 9/1984 | Japan |
| 663622 | 12/1987 | Switzerland |
| 1518996 | 7/1978 | United Kingdom |

Primary Examiner—Gary E. Hollinden
Assistant Examiner—S. Mark Clardy

[57] ABSTRACT

Low cost, rapidly water-dispersible or water-soluble granular compositions containing at least 10% voids and consisting of agglomerates comprised of pesticidal particles bonded together by solid bridges of a water-soluble heat-activated binder.

16 Claims, No Drawings

WATER-DISPERSIBLE OR WATER-SOLUBLE PESTICIDE GRANDULES FROM HEAT-ACTIVATED BINDERS

BACKGROUND OF THE INVENTION

In general, water-dispersible or water-soluble granular compositions are prepared by (1) processes involving aqueous (or solvent) spraying and subsequent drying such as pan or fluidized bed granulation, high intensity mixing, granulation, spray drying, or by spraying the active material (or solution thereof) upon a preformed carrier or (2) processes involving compaction such as briquetting, tabletting, and extrusion.

Japanese Patent Application No. 52/30577 discloses slow-release agrochemical-urea fertilizers which are formed from liquid or organic solvent solutions of agrochemicals, polyoxyethylene nonionic surfactants, and urea.

U.S. Pat. No. 4,707,287 is directed to the protection of certain enzymes from a peroxyacid bleach granulate and discloses an improved granulate enzyme compositions compiling core of enzyme material and a protective coating comprising an alkaline buffer salt. This patent broadly mentions the term "alkylarylethoxylates" among many others as potential waxy substances used as granulating agents, but there is no teaching of any of the specific heat-activated binders of the instant invention.

SUMMARY OF THE INVENTION

This invention comprises a low cost, rapidly water-dispersible or water-soluble pesticidal granular composition which is comprised of agglomerates consisting essentially of solid pesticidal particles bound together by solid bridges of a water-soluble heat activated binder (HAB). The granular composition contains at least about 10% voids (preferably 20% or greater) and comprises by weight based on the total weight of the composition;

(1) 5 to 95% and preferably 20–80% of pesticidal particles or a mixture of pesticidal particles having a size in the range of 1–50 microns or larger if the pesticide is water-soluble; in combination with or held together by solid bridges of (2) 5 to 40% and preferably 10–30% of a heat activated, water-soluble binder (HAB) having one or more components wherein said binder meets the following five criteria:
  (i) has a melting point range within 40°–120° C., and preferably 45° to 100° C.;
  (ii) has a hydrophile/lipophile balance (HLB) of about 14 to 19, preferably 16–19;
  (iii) dissolves in mildly-agitated water in 60 min. or less, preferably 50 min. or less;
  (iv) has a melt viscosity of at least about 200 centipoise (cps); preferably 1,000 cps or greater, and most preferred 2,000 cps or greater; and
  (v) has a difference of 5° C., and preferably 3° C. or less between the softening point and onset of solidification; and optionally (3) one or more additives selected from the group consisting of
  (i) wicking, physically swelling, or gas-producing disintegrants;
  (ii) anti-caking agents;
  (iii) chemical stabilizers;
  (iv) co-binders; and
  (v) surfactants (wetting agents or dispersants)

such that said composition rapidly forms a high quality dispersion (or solution) in water, is attrition resistant (non-dusty), chemically stable, and non-caking. The agglomerates or granules are 150–4000 microns and preferably 250–1500 microns in size.

DETAILED DESCRIPTION OF THE INVENTION

The most common method of applying agricultural pesticides involves their dilution in a solvent or non-solvent liquid in a mix tank followed by spraying of the resulting solution or dispersion. Because of the increasing costs of non-aqueous solvents and the toxicity of some of them, formulations involving water-soluble or water-dispersible granules have become increasingly popular. In such formulations, the dispersed particles formed on dilution should be no greater than 50 microns in their largest dimension to avoid nozzle pluggage or premature settling which results in uneven application of the pesticide. Consequently, it is necessary that all of the components of the formulated product rapidly and completely disperse or dissolve in the dilution water.

Conventional methods for the preparation of water-soluble or water-dispersible granules involve (1) solvent spraying such as fluidized bed or pan granulation techniques or the impregnation of an active pesticide agent on preformed carrier granules or (2) compaction such as tabletting or extrusion. Granules prepared by bed or pan granulation are generally sprayable upon dilution with water, while the impregnated or compacted compositions are usually applied dry and mechanically, for example, using spreaders. The solvent spraying processes can yield granules which are rapidly water-dispersible but are expensive, due to the drying step and extensive, space-consuming equipment required. The granules produced from the compaction processes are generally slow in water dispersion. Furthermore, both of these processes often require specialized technology for their operation.

Often it is desirable to use mixtures of two or more pesticides of different functions, e.g., a mixture of a herbicide and an insecticide, to provide broad spectrum control over a variety of weeds and/or undesirable organisms. However, some of the individual components are physically or chemically incompatible as mixtures, especially in long-term storage. For example, carbamate insecticides are generally unstable in the presence of alkaline components and sulfonylurea herbicides are known to be unstable in the presence of acidic materials. The chemical incompatibility can be due to an impurity present in the complementary pesticide and not the bioactive component itself. For these reasons it would be desirable to have a sprayable, formulated product consisting of particles or granules wherein potentially incompatable, active components are physically separated.

The present invention comprises low cost, rapidly water-dispersible or water-soluble granular compositions consisting of agglomerates comprised of pesticidal particles bonded together by solid bridges of the heat-activated binder (HAB). The granules have 10% voids or more, and have a preferred size of 150 to 4,000 microns. The preferred size of pesticidal particles is 1 to 50 microns, especially for pesticides with low water-solubility, to promote water dispersion, avoid premature settling, and avoid nozzle/screen pluggage during tank-mixing or application in the field. Water-soluble pesticidal particles may be larger.

The granular compositions of this invention display a break-up time of three minutes or less in water, good aqueous dispersion properties with a long tube sedimentation value of 0.02 mL or less, attrition of 33% or less, and are preferably non-caking after 100 hours at 45° C. under a pressure of 3.5 Kg/cm$^2$.

The granules can be comprised of mixtures of pesticidal particles which are ordinarily chemically incompatible (e.g., in a conventional granule made by water spraying, such as fluid bed or pan granulation) because (1) the pesticidal particles can be physically separated from each other via HAB bridges; and (2) water is not required during granulation/drying.

Advantages of the present granules include potential incorporation of incompatible pesticides in the same granule and low cost. The process used to prepare these granules is simple and does not require specialized technology. It utilizes readily available, compact equipment. The process does not require extensive dust collection systems nor a space-consuming and expensive drying operation.

The compositions of this invention can be prepared by several processes (either in a batch or continuous mode) including the processes wherein (1) the pesticidal particles, the HAB particles and optional particulate additives are tumbled/mixed and heat is applied externally until the granules have grown to the desired size, following which the heat is shut off and the granules are allowed to cool while still tumbling or sitting in a separate container; or where (2) the pesticidal particles, HAB, and optional particulate additives are intensely sheared/mixed such that frictional heat melts the HAB thereby effecting granulation following which the aggregates are then cooled; or where (3) the pesticidal particles and optional particulate additives are tumbled/mixed and are sprayed with the heat-activated binder which has been pre-heated and is in a molten state following which the resulting agglomerates are cooled.

Processes (1) and (3), involving gentle tumbling/mixing, can be carried out, e.g. in a heated fluidized bed, a heated blender (e.g., paddle or ribbon type blenders, vee-blenders, zig-zag blenders, Lodige® blenders, Nauta® mixers) or a heated pan or drum granulator. Process (3) may not require additional heat other than that needed to melt the HAB for spraying. Subsequent cooling of the resulting agglomerates is done either in or outside of the processing vessel. Process (2) involving high intensity mixing/shearing can be carried out e.g., in Schugi® or turbulator-type vessels. In Process (1) a preferred method of preparing the initial mixture of particulates before granulation is to mill the pesticidal active plus additives and then mix (e.g., via tumbling) with HAB particulates (e.g., of a size 500–1,000 microns). Separation of pesticides can be enhanced and incompatibility then reduced (especially when one active is present in minor proportions) by forming granules from a particulate premix of the major active component, HAB, and additives, followed by introduction of the minor active component (and optionally additional HAB), while the granules are hot so as to imbed the second active particulates in a HAB layer on the surface of the first granules.

The term "pesticide" is intended to refer to biologically active compositions containing chemicals which are effective in killing pests or preventing or controlling their growth. These chemicals are commonly known as herbicides, fungicides, insecticides, nematocides, acaricides, miticides, virucides, algicides, bactericides, plant growth regulants and their agriculturally suitable salts. Preferred are those pesticides that have melting points above 80° C.; more preferred are pesticides that melt above 100° C. The preferred size of the pesticidal particles used in this invention is 1 to 50 microns. Examples of suitable pesticides are listed below in Table 1.

TABLE 1

| Cm-Cmpd. No. | Common Name | m.p.(°C.) | Chemical Name |
|---|---|---|---|
| | | HERBICIDES | |
| 1 | acifluorfen | 142–160 | 5-[-chloro-4-(trifluoro methyl)phenoxyl-2-nitro-benzoic acid |
| 2 | asulam | 142–144 | methyl [(4-aminophenyl)-sulfonyl]carbamate |
| 3 | atrazine | 175–177 | 6-chloro-N-ethyl-N'-(1-methylethyl)-1,3,5-triazine-2,4-diamine |
| 4 | bensulfuron methyl | 185–188 | 2-[[[[(4,6-dimethoxy-2-pyrimidinyl)aminol}-carbonyl]amino]sulfonyl]-methyl]benzoic acid, methyl ester |
| 5 | bentazon | 137–139 | 3-(1-methylethyl)-(1H)-2,1,3-benzothiadiazin-4(3H)-one, 2,2-di-oxide |
| 6 | bromacil | 158–159 | 5-bromo-6-methyl-3-(1-methyl-propyl)-2,4(1H,3H)pyrimi-dinedione |
| 7 | bromoxynil | 194–195 | 3,5-dibromo-4-hydroxybenzo-nitrile |
| 8 | chloramben | 200–201 | 3-amino-2,5-dichlorobenzoic acid |
| 9 | chlorimuron ethyl | >100 | 2-[[[[(4-chloro-6-methoxy-2-pyrimidinyl)amino]carbonyl]-amino]sulfonyl]benzoic acid, ethyl ester |
| 10 | chloroxuron | 151–152 | N'-[4-(4-chlorophenoxy)-phenyl]N,N-dimethylurea |
| 11 | chlorsulfuron | 174–178 | 2-chloro-N-[[(4-methoxy-6-methyl-1,3,5-triazin-2-yl)-amino]carbonyl]benzene-sulfonamide |
| 12 | chlortoluron | 147–148 | N'-(3-chloro-4-methylphenyl)-N,N-dimethylurea |
| 13 | clomazone | oil | 2-[(2-chlorophenyl)methyl]-4,4-dimethyl-3-isoxazoli-dinone |
| 14 | cyanazine | 166–167 | 2-[[(4-chloro-6-(ethylamino)-1,3,5-triazin-2-yl]amino]-2-methylpropanenitrile |
| 15 | dazomet | 104–105 | tetrahydro-3,5-dimethyl-2H-1,3,5-thiadiazine-2-thione |
| 16 | desmediphan | 120 | ethyl [3-[[(phenylamino)-carbonyl]oxy]-phenyl]-carbamate |
| 17 | dicamba | 114–116 | 3,6-dichloro-2-methoxy-benzoic acid |
| 18 | dichlobenil | 139–145 | 2,6-dichloro-benzonitrile |
| 19 | dichlorprop | 117–118 | (±)-2-(2,4-dichloro-phenoxy)-propanoic acid |
| 20 | diphenamid | 134–135 | N,N-dimethyl-α-phenylbenzene-acetamide |
| 21 | dipropetryn | 104–106 | 6-(ethylthio)-N,N'-bis(1-methylethyl)-1,3,5-triazine-2,4-diamine |
| 22 | diuron | 158–159 | N'-(3,4-dichlorophenyl)-N,N-dimethylurea |
| 23 | thiameturon | >100 | 3-[[[[(4-methoxy-6-methyl-1,3,5-triazin-2-yl)amino]-carbonyl]amino]sulfonyl]- |

TABLE 1-continued

| Cm-Cmpd. No. | Common Name | m.p.(°C.) | Chemical Name |
|---|---|---|---|
| 24 | — | >100 | 2-thiophenecarboxylic acid, methyl ester 2-[[[[(N-(4-methoxy-6-methyl-1,3,5-triazine-2-yl)-N-methylamino]carbonyl]-amino]sulfonyl]benzoic acid, methyl ester |
| 25 | fenac | 156 | 2,3,6-trichlorobenzeneacetic acid |
| 26 | fenuron | 133–134 | N,N-dimethyl-N'-phenylurea |
| 27 | fluometuron | 163–164 | N,N-dimethyl-N'-[3-(trifluoromethyl)phenyl]urea |
| 28 | fluridone | 151–154 | 1-methyl-3-phenyl-5-[3-(trifluoromethyl)phenyl]-4(1H)-pyridinone |
| 29 | fomesafen | 220–221 | 5-[2-chloro-4-(trifluoromethyl)phenoxy]-N-(methylsulfonyl)-2-nitrobenzamide |
| 30 | glyphosate | 200 | N-(phosphonomethyl)glycine |
| 31 | hexazinone | 115–117 | 3-cyclohexyl-6-(dimethylamino)-1-methyl-1,3,5-triazine-2,4(1H,3H)-dione |
| 32 | imazamethabenz | >100 | 6-(4-isopropyl-4-methyl-5-oxo-2-imidazolin-2-yl)-m-toluic acid, methyl ester and 6-(4-isopropyl-4-methyl 5-ozo-2-imidazolin-2-yl)-p-toluic acid, methyl ester |
| 33 | imazaquin | 219–222 | 2-[4,5-dihydro-4-methyl-4-(1-methylethyl)-5-ozo-1H-imidazol-2-yl]-3-quinoline-carboxylic acid |
| 34 | imazethapyr | 172–175 | (±)-2-[4,5-dihydro-4-methyl-4-(1-methylethyl)-5-oxo-1H-imidazol-2-yl]-5-ethyl-3-pyridinecarboxylic acid |
| 35 | ioxynil | 209 | 4-hydroxy-3,5-diiodobenzonitrile |
| 36 | isoproturon | 155–156 | N-(4-isopropylphenyl)-N',N'-dimethylurea |
| 37 | isouron | 119–120 | N'-[5-(1,1-dimethylethyl)-3-isoxazolyl]-N,N-dimethylurea |
| 38 | isoxaben | 176–179 | N-[3-(1-ethyl-1-methyl-propyl)-5-isoxazolyl]-2,6-dimethoxy-benzamide |
| 39 | karbutilate | 176–178 | 3-[[(dimethylamino)carbonyl]-amino]phenyl-(1,1-dimethyl-ethyl) carbamate |
| 40 | lenacil | 316–317 | 3-cyclohexyl-6,7-dihydro-1H-cyclopenta-pyrimidine-2,4-(3H,5H)dione |
| 41 | MCPA | 100–115 | (4-chloro-2-methyl-phenoxy)-acetic acid |
| 42 | MCPB | 100 | 4-(4-chloro-2-methyl-phenoxy)-butanoic acid |
| 43 | mefluidide | 183–185 | N-([2,4-dimethyl-5-[[(trifluoromethyl)sulfonyl]-amino]phenyl]acetamide |
| 44 | methabenz-thiazuron | 119–120 | 1,3-dimethyl-3-(2-benzothiazolyl)urea |
| 45 | mothazole | 123–124 | 2-(3,4-dichlorophenyl)-4-methyl-1,2,4-oxadiazol-idine-3,5-dione |
| 46 | metribuzin | 125–126 | 4-amino-6-(1,1-dimethyl-ethyl)-3-(methylthio)-1,2,4-triazin-5(4H)-one |
| 47 | metsulfuron methyl | 163–166 | 2-[[[[(4-methoxy-6-methyl-1,3,5-triazin-2-yl]amino]-carbanyl]amino]sulfonyl]-benzoic acid, methyl ester |
| 48 | monuron | 174–175 | N'-(4-chlorophenyl)-N,N-dimethylurea |
| 49 | naptalam | 185 | 2-[(l-naphthalenylamino)-carbonyl]benzoic acid |
| 50 | neburon | 102–103 | 1-butyl-3-(3,4-dichloro-phenyl)-1-methylurea |
| 51 | nitralin | 151–152 | 4-(methylsulfonyl)-2,6-dinitro-N,N-dipropyl-aniline |
| 52 | norflurazon | 174–180 | 4-chloro-S-(methyl-amino)-2-[3-(trifluoro-methyl)phenyl]-3(2H)-pyridazinone |
| 53 | oryzalin | 141–142 | 4-(dipropylamino)-3,5-dinitrobenzenesulfonamide |
| 54 | perfluidone | 142–144 | 1,1,1-trifluoro-N-[2-methyl-4-(phenylsulfonyl)phenyl]-methanesulfonamide |
| 55 | phenmedipham | 143–144 | 3-[(methoxycarbonyl)amino]-phenyl (3-methylphenyl)-carbamate |
| 56 | picloram | >215 (DEC) | 4-amino-3,5,6-trichloro-2-pyridinecarboxylic acid |
| 57 | prometryn | 118–120 | N,N'-bis(1-methylethyl)-6-(methylthio)-1,3,5-triazine-2,4-diamine |
| 58 | pronamide | 155–156 | 3,5-dichloro-N-(1,1-dimethyl-2-propynyl)benzamide |
| 59 | propazine | 212–214 | 6-chloro-N,N'-bis(1-methyl-ethyl)-1,3,5-triazine-2,4-diamine |
| 60 | pyrazon | 205–206 | 5-amino-4-chloro-2-phenyl-3(2H)pyridazinone |
| 61 | siduron | 133–138 | N-(2-methylcyclohexyl)-N'-phenylurea |
| 62 | simazine | 225–227 | 6-chloro-N,N'-diethyl-1,3,5-triazine-2,4-diamine |
| 63 | sulfometuron methyl | 182–189 | 2-[[[[(4,6-dimethyl-2-pyrimidinyl)amino]carbonl]-amino]sulfonyl]benzoic acid, methyl ester |
| 64 | tebuthiuron | 161–164 | N-[5-(1,1-dimethylethyl)-1,3,4-thiadiazol-2-yl]-N,N'-dimethylurea |
| 65 | terbacil | 175–177 | 5-chloro-3-(1,1-dimethyl-ethyl)-6-methyl-2,4(1H,3E)-pyrimidinedione |
| 66 | terbuthyl-azine | 177–179 | 2-(tert-butylamino)-4-chloro-6-(ethyl-amino)-s-triazine |
| 67 | terbutryn | 104–105 | N-(1,1-dimethylethyl)-N'-ethyl-6-(methylthio)-1,3,5-triazine-2,4-diamine |
| 68 | triclopyr | 148–150 | [(3,5,6-trichloro-2-pyri-dinyl)oxy]acetic acid |
| 69 | 2,4-D | 140 | (2,4-dichlorophenoxy)acetic acid |
| 70 | 2,4-DB | 119–120 | 4-(2,4-dichlorophenoxy)-butanoic acid |
| 71 | triasulfuron | >100 | (3-(6-methoxy-4-methyl-1,3,5-triazin-2-yl)-1-[2-(2-chloroethoxy)phenylsulfonyl] urea |
| 72 | primisulfuron | >100 | [2-/3-(4,6-bis(difluoro-methoxypyrimidin-2-yl-ureidosulfonyl)benzoic acid methylester] |
| 73 | — | >100 | [2-/3-(4,6-bis(difluoro-methoxy)-pyrimidin-2-yl)-ureidosulfonyl)-benzoic acid methylester] |
| 74 | NC-311 | 170–172 | [5-pyrazolesulfonamide, N-[(4-methoxy-6-methyl-pyrimidine-2-yl)-amino-carbonyl)-4-methoxy-carbonyl-1-methyl-] |
| 75 | — | 160–162 | N-[[(4,6-dimethoxy-2-pyrimidinyl)amino]carbonyl]-3-(ethylsulfonyl)-2-pyridinesulfonamide |
| 76 | — | 152–159 | 2-[[[[(4,6-dimethoxy-2-pyrimidinyl)amino]carbonyl]-amino]sulfonyl]-N,N-dimethyl-3-pyridine-carboxamide |
| 77 | — | 204–206 | Methyl 2-[[[[4-ethoxy-6-(methylamino)-1,3,5-triazin- |

TABLE 1-continued

| Cm-Cmpd. No. | Common Name | m.p.(°C.) | Chemical Name |
|---|---|---|---|
| | | | 2-yl]aminolcarbonyl]amino]-sulfonyl]benzoate |
| FUNGICIDES | | | |
| 78 | carbendazim | 302–307 | methyl 2-benzimidazole-carbamate |
| 79 | thiuram | 146 | tetramethylthiuram disulfide |
| 80 | dodine | 136 | a-dodecylguanidine acetate |
| 81 | chloroneb | 133–135 | 1,4-dichloro-2,5-dimethoxybenzene |
| 82 | cymoxanil | 160–161 | 2-cyano-N-ethylcarbamoyl-2-methoxyiminoacetamide |
| 83 | captan | 178 | N-trichloromethylthiotetrahydrophthalamide |
| 84 | folpet | 177 | N-trichloromethylthiophthalimide |
| 85 | thiophanate-methyl | 195 | dimethyl 4,4'-(o-phenylene)-bis(3-thioallophanate) |
| 86 | thiabendazole | 304–305 | 2-(thiazol-4-yl)benzimidazole |
| 87 | chlorothalonil | 240–241 | tetrachloroisophthalonitrile |
| 88 | dichloran | 195 | 2,6-dichloro-4-nitroaniline |
| 89 | captafol | 160–161 | cis-N-[1,1,2,2-tetrachloroethyl)thio]cyclohex-4-ene-1,2- dicarboximide |
| 90 | iprodione | 133–136 | 3-(3,5-dichlorophenyl)-N-(1-methylethyl)-2,4-dioxo-1-imidazolidine carboxamide |
| 91 | vinclozolin | 108 | 3-(3,5-dichlorophenyl)-5-ethenyl-5-methyl-2,4-oxazolidinedione |
| 92 | kasugamycin | 202–204 (DEC) | kasugamycin |
| 93 | triadimenol | 121–127 | beta-(4-cllorophenoxy)-a-(1,1-dimethylethyl)-1-H-1,2,4-triazol-1-ethanol |
| 94 | flutriafol | 130 | +-a-(2-fluorophenyl-a-(4-fluorophenyl)-1H-1,2,4-triazole-1-ethanol |
| 95 | flusilazol | 52–53 HCl 201–203 | 1-[[bis(4-fluorophenyl)-methylsilyl)methyl]]-1H-1,2,4-triazole |
| 96 | hexaconazole | 111 | (+/−)-a-butyl-a-(2,4-di chlorophenyl)-1H-1,2,4-triazole-1-ethanol |
| 97 | fenarimol | 117–119 | a-(2-chlorophenyl)-a-(4-chlorophenyl)-5-pyridinemethanol |
| BACTERICIDES | | | |
| 98 | oxytetracycline dihydrate | 181–182 (DEC) | oxytetracycline dehydrate |
| ACARICIDES | | | |
| 99 | hexathiazox | 108–109 | trans-5-(4-chlorophenyl)-N-cyclohexyl-4-methyl-2-oxo-3-thiazolidinecarboxamide |
| 100 | oxythioquinox | 169–170 | 6-methyl-1,3-dithiolo-[2,3-B]quinonolin-2-one |
| 101 | dienochlor | 122–123 | bis(pentachloro-2,4-cyclopentadien-1-yl) |
| 102 | cyhexatin | 245 | tricyclohexyltin hydroxide |
| INSECTICIDES | | | |
| 103 | carbofuran | 150–152 | methylcarbamic acid, ester with 2,3-dihydro-2,2-dimethyl-7-benzofuranol |
| 104 | carbaryl | 142 | methylcarbamic acid, ester with a-naphthol |
| 105 | thiodicarb | 173–174 | dimethyl N,N'-[thiobis-(N-methylimmo)carbonyloxy]]-bis(ethanimidothioate] |
| 106 | deltamethrin | 98–101 | a-cyano-3-phenoxybenzyl-cis 3-(2,2-dibromovinyl)-2,2-dimethylcyclopropane carboxylate |

The term "heat-activated binder" refers to any surface active material comprised of one or more components which dissolve rapidly in water, have some viscosity near the melting point for tackiness, and are thus capable of acting as a binder when heat is applied. At some elevated temperature, the binder softens and melts, thereby becoming sticky enough to bind the pesticidal particles into granules. A more preferred amount of binder used in this invention is 10–30% by weight based on the total weight of the composition. A more preferred melting point range for the binders of this invention is 45° C. to 100° C. Examples of suitable heat-activated binders, which are not intended to be limiting, are ethylene oxide/propylene oxide copolymers and polyethoxylated dinonylphenol.

The HAB can be a single component or multi-components which are mixed in the solid state, co-melted or co-dissolved. Preferred single component HAB's are ethylene oxide/propylene oxide copolymers and polyethoxylated dinonylphenol. Specifically preferred single components are block copolymers of ethylene oxide/propylene oxide, where 80% is ethylene oxide and 20% is propylene oxide, and polyethoxylated dinonylphenol with 150 ethylene oxide units. The preferred copolymer has an HLB of 16 and a melting point of about 45° to 61° C. The preferred dinonylphenol derivative has an HLB of about 19 and a melting point of about 48° to 63° C.

The HAB must meet the following five criteria:
(1) have a melting point range within 40° to 120° C.;
(2) be water-soluble with a hydrophile/lipophile balance (HLB) of about 14 to 19;
(3) dissolve in mildly-agitated water in 50 minutes or less;
(4) have a melt viscosity of at least 200 cps; and
(5) have a difference of 5° C. or less between the softening point and onset of solidification.

The use of a HAB having a very low melting point can lead to caking of the granules, while use of a HAB having a very high melting point can require a temperature sufficiently high so that decomposition of the pesticide or other components can occur during granulation.

Surface activity as measured by the critical HLB range is necessary to provide good bonding of the HAB to pesticidal particles and rapid wetting at the onset of bridge dissolution when the granules are placed in water. Materials which have too low an HLB are not completely water-soluble.

The dissolution rate in water is very important, since factors other than HLB affect dissolution, e.g., viscosity of the hydrated HAB and its tendency to form a gel-like layer when in contact with mildly or non-agitated water.

The use of a HAB having the specified melt viscosity and minimum difference between softening and solidification temperatures is necessary so that it will be tacky enough to effect agglomeration of pesticidal particles near the melting point of the HAB.

Additives, many of which are commonly used in conventional granules, may optionally be used in HAB granules. Examples include:

(1) disintegrants which wick in water, physically expand, or produce gas to aid break-up of the granule. Non-limiting examples of suitable disintegrants include cross-linked polyvinyl pyrrolidone, microcrystalline cellulose, cross-linked sodium carboxymethyl cellulose, salts of polyacrylates of methacrylates, and the combination of sodium or potassium bicarbonates or carbonates with acids such as citric or fumaric acid, used alone or in combination, at levels of up to 30% by weight based on the total weight of the composition;

(2) anticaking agents to prevent clumping of granules when stored under hot warehouse conditions. Non-limiting examples of suitable anticaking agents include sodium or ammonium phosphates, sodium carbonate or bicarbonate, sodium acetate, sodium metasilicate, magnesium or zinc sulfates, magnesium hydroxide (all optionally as hydrates), and sodium alkylsulfosuccinates;

(3) chemical stabilizers to prevent decomposition of the active(s) during storage. Non-limiting examples of suitable chemical stabilizers include alkaline earth or transition metal sulfates such as magnesium, zinc, aluminum, and iron (optionally as hydrates) used at levels of 1–9% by weight based on the total weight of the composition;

(4) co-binders to achieve optimized properties such as increased granulation efficiency or improved anticaking. Up to 50% co-binders such as polyethylene glycols, polyethylene oxide, polyethoxylated fatty acids or alcohols, hydrated inorganics such as sodium silicate, sorbitol, or urea may be used; and (5) surfactants to improve the speed and quality of wetting and dispersion of the granule upon mixing with water. Often dispersing agents are most useful, since the HAB itself has wetting characteristics.

Examples of preferred dispersants include sodium or ammonium salts of sulfonated naphthalene (or methyl naphthalene)-formaldehyde condensates, sodium, calcium, or ammonium salts of ligninsulfonates (optionally polyethoxylated); dialkyl; diolalkynes; sodium taurates; and sodium or ammonium salts of maleic anhydride copolymers.

HAB candidates may be identified by the following tests:

(1) the melting point is measured by DSC (Differential Scanning Calorimetry) at a 5° C./minute heating rate. The onset of the melt should be no lower than 40° C.;

(2) The hydrophile/lipophile balance with a total possible range of 1 to 20 is determined by the method outlined in McCutheon's "Detergents and Emulsifiers", 1971 annual, page 223;

(3) The rate of dissolution in water is determined by the following procedure:

(a) a sample of the test material (0.15 g) is placed in the bottom of a glass graduated cylinder with an inside diameter of 2.8 cm, (b) the cylinder is placed on a steam bath (alternately heated externally with a stream of hot air near the bottom) until the sample is fully melted, (c) the cylinder is placed on a level surface and the sample allowed to solidify upon cooling to 25° C., yielding an even layer in the bottom, (d) water is added (100 mL at 25° C.) to the cylinder and is stirred at 110 rpm with a rectangular metal or plastic paddle having a thickness of 1.5 mm, a width of 18 mm, and a height of 16.5 mm so that the bottom of the paddle is 48 cm above the surface of the solidified sample, and (e) the time for complete dissolution of the sample is noted;

(4) The viscosity at the softening point is calculated using an Arrhenius plot (Ln viscosity vs 1/T).

The plot is derived from experimental viscosity measurements vs temperature using a rotational viscometer operated at a shear rate of 1.16 sec$^{-1}$. Viscosity measurements are taken over at least a 30° C. temperature range whose minimum temperature is within 1° C. of the softening point as measured by DSC.

Another requirement of the melt behavior of HAB candidates is that the onset of softening in the heating curve differs by 5° C. or less from the onset of solidification in the consecutive cooling curve. This parameter is measured using a differential scanning calorimeter (e.g., Du Pont Instruments 1090 Thermal Analyser with model 910 DSC module). One to three milligrams of sample is typically used in a hermetically-sealed coated aluminum pan. The heating curve endotherm is observed at 5° C./minute, while the cooling curve exotherm is observed at 1° C./minute. Typically a sample is heated from 25° C. to 100° C. to 120° C. and then allowed to cool back to 25° C. It should be noted that a given HAB can exhibit a broad melting behavior (usually 12° to 16° C. from softening to full melt).

Granules of this invention have at least 10% voids and preferably at least 20%. The upper limit of voids is set by the fragility (high attrition) of the granule. Determination of voidage is accomplished by pycnometer measurements of the starting premix powder and the final HAB granules, using a paraffin oil. Alternately, helium porosimetry may be used. Voids are important to speed penetration of water into the granule and thus aid break-up in the mix tank.

The granules also exhibit break-up times in water of less than 3 minutes and preferably less than 2. Break-up time is measured by adding a sample of the granules (0.5 g, 250 to 1410 microns) to a 100 mL graduated cylinder [internal height after stoppering is 22.5 cm; I.D. is 28 mm] containing 90 mL of distilled water at 25° C., following which the cylinder is clamped in the center, stoppered, and rotated about the center at 8 rpm until the sample is completely broken up in the water.

Formation of a high quality aqueous dispersion is also a desirable property and is determined by the long tube sedimentation test in U.S. Pat. No. 3,920,442 (Col. 9, lines 1 to 39). Acceptable values correspond to 0.02 mL, preferably 0.01 mL of solids after 5 minutes of settling.

The granules should exhibit low attrition characteristics which can be determined by the attrition test in U.S. Pat. No. 3,920,442 (Col. 8, lines 5 to 48). The test is modified to use test samples of the commercial granule size (e.g., 250 to 1410 microns). Attrition values of less than 40% and preferably less than 30% are acceptable.

The granules should also resist caking. This property is determined by taping a stainless steel disc (0.9 mm thick × 51 mm diameter) flush with the bottom of a glass cylinder (46.5 mm i.d. × 75 mm length × 51 mm thickness) following which the granular sample (20 g) is delivered to the cylinder assembly and leveled, and a second stainless steel disc (0.9 mm thick × 44.5 mm diameter) is placed on the top of the granules.

A 400 g weight (45 mm diameter or less) is then placed on top of the inner disc, and the entire assembly is placed in an oven for 100 hours at 45° C. (preferably 55° C.) following which the assembly is removed from the oven, the weight removed, and the sample allowed to cool to room temperature. The bottom disc is then detached and if the sample flows out of the cylinder, the resistance to caking is excellent, and if the sample remains in the cylinder, the cake is removed, placed onto a flat surface and a penetrometer is used with a single-edged razor to measure the minimum force necessary to cleave the cake.

Cakes requiring a force of less than 100 g, and preferably less than 5 g are acceptable.

The following examples are presented to illustrate, but not to restrict, this invention.

| Definitions of Ingredients Used in Examples | |
|---|---|
| Name | Identity |
| Macol ® DNP 150 (Mazer Chemicals) | polyethylated dinonylphenol (150 ethylene oxide units) Melt behavior: melting point - softening point 48° C.; finish 63° C. difference between softening point and onset of solidification = 20° C. melt viscosity - about 1,900 cps at softening point Dissolution Rate: 19 minutes HLB: 19 |
| Pluronic ® F108 (BASF) | ethylene oxide/propylene oxide block copolymer with 80% ethylene oxide and 20% propylene oxide units Melt behavior: melting point - softening point 45° C.; finish 61° C. difference between softening point and onset of solidification = 0° C. melt viscosity: at softening point about 26,500 centipoises (cps) Dissolution Rate: 50 minutes HLB: 16 |
| Hodag ® E100 (Hodag Chemical Corp.) | a 100 mole ethoxylate of nonylphenol Melt behavior: melting point - softening point 40° C.; finish point 64° C. difference between softening point and onset of solidification = 0° C. melt viscosity at softening point = 1,100 cps Dissolution Rate: 20 minutes HLB: 19 |
| Iconol ® OP-40 (BASF) | a 40 mole ethoxylate of octylphenol Melt behavior: melting point - softening point = 40° C.; finish = 55° C. difference between softening point and onset of solidification = 3° C. viscosity at softening point about 700 cps Dissolution Rate: 18 minutes HLB: 18 |
| Polyplasdone ® XL-10 (GAF) | Cross-linked polyvinyl pyrrolidone |
| Avicel ® PH-105 (FMC) | microcrystalline cellulose |
| AC-DI-SOL ® (FMC) | Cross-linked sodium carboxymethyl cellulose |
| Morwet ® D425 (Desoto) | sodium napthalene sulfonate formaldehyde condensate |
| Morwet ® EFW (Desoto) | sodium alkyl naphthalene sulfonate |
| Lignosol ® TSF (Reed) | ammonium lignosulfonate |
| Monawet ® MB100 (Mona) | sodium dibutylsulfosuccinate |
| Aerosol ® A196 (Amer. Cy.) | sodium dicyclohexylsulfo-succinate (+ 15% sodium benzoate) |

-continued

| Definitions of Ingredients Used in Examples | |
|---|---|
| Name | Identity |
| Explotab ® (Edward Mendell Co.) | sodium starch glycolate |
| Triton ® AG-120 (R & H) | polyethoxylated nonyl phenol absorbed on silica |
| Triton ® X-120 (R & H) | polyethoxylaed nonyl phenol absorbed in $MgCo_3$ |

EXAMPLE 1

All ingredients below (with the exception of the Macol ®)were mixed and then milled on a high intensity rotary shearing mill. The resultant mixture was then mixed with Macol ® DNP 150 (<840 microns) to form a premix for granulation. A 150 g portion of the premix was placed in a fluidized bed and heated air was applied to the granules. When the temperature of the granules reached 70° C. (about 12 minutes) the heat was shut off and the granules allowed to cool while still fluidized by unheated air. A 70% yield of a 250 to 1410 micron spherical granules was realized. The premix formulation and resulting properties of the granules are given below.

| Premix Formulation | |
|---|---|
|  | Weight Percent |
| Chlorsulfuron | 75.0 |
| Macol ® DNP150 | 10.0 |
| Anhydrous $MgSO_4$ | 6.0 |
| Polyplasdone ® XL-10 + Impurities | 9.0 |
| Properties of Granules (250 to 1410 microns) | |
| % Attrition | 21.0% |
| 25° C. Break-up Time in water | 75.0 sec |
| OC Break-up Time in water | 102.0 sec |
| 25° C. Break-up Time - in 28-0-0 Liquid Fertilizer | 214.0 sec |
| 55° C. Caking | 0.0 g |
| Long Tube Sedimentation | Trace |
| Long Tube Sedimentation (1 wk/55° C.) | .003 |
| Assay (% chlorsulfuron) | |
| Control | 72.9% |
| 1 wk/55° C. | 70.0% |

EXAMPLE 2

Example 1 was repeated except that the premix without binder was hammer-milled.

| Premix Formulation | Example 2 |
|---|---|
| Chlorsulfuron Tech (%) | 77 |
| Macol ® DNP150 (%) | 10 |
| $MgSO_4.7H_2O$ (%) | 3 |
| $ZnSO_4.7H_2O$ (%) | 3 |
| Polyplasdone ® XL-10 (%) | 7 |
| Avicel ® PH-105 (%) | — |
| AC-DI-SOL ® (%) | — |
| Premix Charge (GM) | 1934 |
| Conversion (%) | 73 |
| Attrition (%) | 29 |
| Long tube sedimentation | 0.002 |
| Long tube sedimentation (1 wk/50° C.) | 0.002 |
| 25° C. $H_2O$ Break-up (sec) | 83 |

-continued

| Premix Formulation | Example 2 |
| --- | --- |
| 0° C. H₂O Break-up (sec) | 107 |
| 25° C. 28-0- Break-up (sec) | 250 |
| 55° C. Caking (GM Force) | 0 |

EXAMPLE 3

Approximately 73.84 g of 2,4-D, Na salt and 1.16 g of 2-[[N-(4-methoxy-6-methyl-1,3,5-triazin-2-yl)-N-methylamino]carbonyl]amino]sulfonyl]benzoic acid, methyl ester, Na salt were milled together as in Example 1. This material was then blended with 25 g of Macol ® DNP-150 (<840 microns). The mixture was then added to a laboratory double cone blender and heated with a heat gun to 77° C., whereupon granulation was observed. The heat was removed and the granules allowed to cool to 50° C. then removed from the blender. Approximately 97.3 g were recovered with 88.3% being between 250 and 1410 microns in size. The physical properties of the granules were: long tube sedimentation (5 minute reading) 0 ml, attrition—33.7%, break-up time in 25° C. water—2.17 minutes and bulk density—0.50 g/ml.

The granules exhibited good chemical stability upon aging, also with no loss of the above physical properties.

EXAMPLE 4

Approximately 72.86 g 2,4-D, Na salt, 1.14 g of 2-[[N-(4-methoxy-6-methyl-1,3,5-triazin-2-yl)-N-methylamino]carbonyl]amino]sulfonyl]benzoic acid, methyl ester, Na salt and 1 g NaHCO₃ were milled together as in Example 1. This mixture was then blended with 25 g Macol ® DNP-150 (<840 microns). The procedure of Example 3 was then followed to produce granules. Approximately 93.4 g were recovered with 90.9% being between 250 and 1410 microns. The physical properties of the as made granules were: long tube sedimentation (5 minute reading)—trace, bulk density—0.5 g/ml, attrition—37.5%, and break-up time in 25° C. water—2.18 minutes. The properties after aging at 45° C. for 3 weeks were: long tube sedimentation (5 minute reading)—trace, bulk density—0.5 g/ml, attrition—36.8%, break-up time in 25° C. water—2.19 minutes. As in Example 3, these granules also maintained good chemical stability on aging.

EXAMPLE 5

Approximately 1480 g methabenzthiazuron, 9.80 g ammonium salt of chlorsulfuron (technical), 5.16 g Sellogen ® HR, 6.88 g Petro ® D425, 12.90 g diammonium hydrogen phosphate, 137.26 g kaolin clay, 40 g MgSO₄, and 48 g Polyplasdone ® XL-10 were milled in an ACM mill at 90 g/min feed rate, rotor speed of 11,000 rpms, classifier speed of 6,000 rpms and as air flow of 50 cfm. Approximately 1643 g of milled material was recovered from the mill. Three 600 g batches were granulated in a laboratory 2.2 liter vee blender by combining 522 g of the milled material and 78 g of less than 500 micron Pluronic ® F108. This material was blended and heated as in Example 3 to 70° C. when granulation was observed. The heat was removed and the granules cooled to 45° C. before removing from the blender. Approximately 1787 g of granules were recovered from the blender with 88.7% being between 250 to 1410 microns in size. The physical properties of the granules were: long tube sedimentation (5 minute reading)—0.015 ml, break-up time in 25° C. water—1.70 minutes, bulk density—0.5 g/ml, and attrition—11.9%. This material passed both the 45° C. and 55° C. caking test.

EXAMPLE 6

The following were hammer-milled:

86.9% Na 2,4-D tech (83% assay as acid)
1.3% 2-[[N-(4-methoxy-6-methyl-1,3,5-triazine-2-yl)-N-methylamino]carbonyl]amino]sulfonyl]benzoic acid, methyl ester, Na salt (92% assay as the free sulfonylurea)
5.9% Morwet ® D425
5.9% Morwet ® EFW The resulting premix was continuously auger fed [62 g/min.] to a 35.6 cm diameter disc agglomerator (56° angle with horizontal) rotating at 30 rpm. Molten Macol ® DNP-150 (95° C.) was sprayed continuously (23 g/minute) onto the premix in the agglomerator using an external mix, air-atomizing, spray nozzle. The Macol ® comprised 25–30% of the total mass of resulting granules. A yield of 61% of 1410 to 1680 micron granules was obtained. The granules had an attrition of 39%, a long tube sedimentation of 0 mL, and a break-up time in 25° C. water of 150 seconds.

EXAMPLE 7

The premix of Example 1 was metered continuously to a 2 liter capacity stainless steel drum (10 cm high × 12 cm diameter) which was rotated at 34 rpm at a 30° angle with the horizontal. The bed of premix on the drum was maintained at 70°–77° C. by heating the external wall of the drum with an infrared lamp. Approximately 89% of granules exiting the drum were 250 to 1410 microns in size. These granules had a long tube sedimentation of 0.01 ml, an attrition of 40%, and a break-up time of 64 seconds in 25° C. water.

EXAMPLE 8

A premix of 20 g of sodium 2,4D (84% assay), 0.5 g 2-[[N-(4-methoxy-6-methyl-1,3-triazin-2-yl)-N-methylamino]carbonyl]amino]sulfonyl]benzoic acid, methyl ester, Na salt (91% assay), and 3.6 g of Macol ® DNP-150 were milled as in Example 1 for two minutes. The dustless contents were then screened, revealing that 61% of the granules produced were in the 149 to 840 micron range and 89% in the 74 to 840 micron range. The long tube sedimentation of the granules in the latter size range was 0 ml, the break-up time in 25° C. water was 90 seconds, and the attrition was 40%. There was 0% decomposition of either active after aging 1 week and 3% decomposition of the sulfonylurea after 2 weeks at 55° C.

EXAMPLE 9

Approximately 100 g of premix was made by combining the following ingredients:

Chlorsulfuron technical 78.5 g
Macol ® DNP-150 12.0 g
ZnSO₄.7H₂O 2.0 g
MgSO₄.7H₂O 2.0 g
Ac-Di-Sol ® 2.75 g
Avicel ® PH-105 2.75 g The premix was milled as in Example 1 to a powder which was then placed in a fluid bed granulator and fluidized with hot air. The bed was gradually heated to 70° C. (9-10 minutes). The granules formed as the binder softened. The heat was removed and the granules were allowed to cool while fluidization was continued. After cooling, the granulated product was sieved. Approximately 76 g of granules were recovered in the 250 to 1410 micron size range which exhibited the following properties.

| | |
|---|---|
| Break-up Time in 25° C. water | 81 seconds |
| Caking (1 day/55° C./3.5 Kg/cm$^2$) | none |
| Assay on sample stored 1 week at −6° C. | 74.4% |
| Assay on sample stored 1 week at 55° C. | 75.8% |
| Long Tube Sedimentation (before and after aging) | 0.005 mL |
| Attrition | 12% |

EXAMPLE 10

100 g of a premix was prepared by combining:

Chlorsulfuron technical 77.0 g
Hodag ® E-100 10.0 g
Anhydrous sodium carbonate 2.0 g
Polyplasdone ® XL-10 2.0 g
Sodium acetate trihydrate 2.75 g The premix was milled and granulated as described in Example 9. Approximately 60 g of 250 to 1410 micron granules were recovered. Break-up times in 25° C. water averaged 91 seconds. There was no caking after 4 days at 55° C.

EXAMPLE 11

100 g of a premix was prepared by combining:

Chlorsulfuron technical 77.0 g
Iconol ® OP-40 10.0 g
Anhydrous sodium carbonate 6.0 g
Polyplasdone ® XL-10 7.0 g
Sodium acetate trihydrate 2.75 g The premix was milled and granulated as described in Example 9. Approximately 57 g of 250 to 1410 micron granules were obtained. The break-up time in 25° C. water was 69 seconds. There was no caking after 4 days at 55° C. Attrition was 34%.

EXAMPLE 12

100 g of a premix was prepared by combining:

Benzoic Acid, 2-[[(4-ethoxy-6-methylamino-1,3,5-triazin-2-yl)aminocarbonyl]aminosulfonyl]methyl ester 77.0 g
Hodag ® E-100 10.0 g
Anhydrous MgSO$_4$ 6.0 g
Polyplasdone ® XL-10 7.0 g The premix was milled and granulated as described in Example 9. Approximately 59 g of 250 to 1410 micron granules were obtained. The break-up time in 25° C. water was 90 seconds. The granules did not cake after 4 days at 55° C. Attrition was 28% and long tube sedimentation was 0.005 ml. Chemical stability was excellent.

EXAMPLE 13

The granulation procedure of Example 5 was repeated, using the following ingredients in the premix:

methabenzthiazuron 1460 g
Chlorsulfuron tech. 10 g
Pluronic ® F108 240 g
MgSO$_4$ 10 g
ZnSO$_4$.7H$_2$O 90 g
Morwet ® D-425 50 g
Avicel ® PH-105 140 g The resulting granules (250 to 1410 microns) were produced in 83% yield and had the following properties: long tube sedimentation—0.015 ml, caking—100 g at 45° C., break-up time in 25° C. water—90 seconds, and attrition—10%.

What is claimed is:

1. A granular composition which comprises by weight based on the total weight of the composition: 5 to 95% of pesticidal particles in combination with 5 to 40% of a water-soluble heat activated binder having a melting point range within 40° to 120° C., a difference of less than 5° C. between the softening point and the onset of solidification, a hydrophile/lipophile balance of about 14 to 19, a dissolution time of not greater than about 50 minutes; and a melt viscosity of at least about 200 cps; and optionally at least one additive selected from the group consisting of
   (i) wicking, physically swelling, or gas-producing disintegrants;
   (ii) anti-caking agents; and
   (iii) chemical stabilizers; and
   (iv) surfactants (wetting or dispersants) agents and mixtures of the foregoing;
wherein said granular composition is characterized by a break-up rate in aqueous medium of less than about 3 minutes.

2. A composition of claim 1 comprising by total weight 20 to 80% of pesticidal particles, and 10 to 30% of the heat activated binder.

3. The composition of claim 1 wherein the difference between the softening point and the onset of solidification is less than 3° C.

4. The composition of claim 2 wherein the difference between the softening point and the onset of solidification is less than 3° C.

5. The composition of claim 1 wherein the melting point range is 45°-100° C.

6. The composition of claim 2 wherein the melting point range is 45°-100° C.

7. The composition of claim 3 wherein the melting point range is 45°-100° C.

8. The composition of claim 2 wherein the hydrophile/lipophile balance is in the range of 16-19.

9. Water-dispersible or water-soluble pesticidal granules which contain at least about 10% voids and comprise agglomerates having a size in the range 250 to 1500 microns which agglomerates are comprised of pesticidal particles having a size in the range of 1 to 50 microns in diameter bonded together by solid bridges of a water-soluble heat-activated binder as described in claim 1.

10. The granules of claim 9 which contain at least about 20% voids.

11. The granules of claim 10 which contain at least about 20% voids and the binder comprises by weight 10 to 30% of the total weight.

12. The granules of claim 11, wherein the hydrophile/lipophile balance of the binder is in the range of 16–19.

13. The composition of claim 1 wherein the binder is selected from the class consisting of polyethoxylated dinonylphenol, ethylene oxide/propylene oxide copolymer and mixtures of the foregoing.

14. The composition of claim 8 wherein the binder is selected from the class consisting of polyethoxylated dinonylphenol, ethylene oxide/propylene oxide copolymer and mixtures of the foregoing.

15. The composition of claim 9 wherein the binder is selected from the class consisting of polyethoxylated dinonylphenol, ethylene oxide/propylene oxide copolymer and mixtures of the foregoing.

16. The composition of claim 12 wherein the binder is selected from the class consisting of polyethoxylated dinonylphenol, ethylene oxide/propylene oxide copolymer and mixtures of the foregoing.

* * * * *

UNITED STATES PATENT AND TRADEMARK OFFICE
CERTIFICATE OF CORRECTION

PATENT NO. : 5,372,989

DATED : December 13, 1994

INVENTOR(S) : William L. Geigle et al

It is certified that error appears in the above-identified patent and that said Letters Patent is hereby corrected as shown below:

Column 4, line 12 (Table 1):

Delete from left column heading "Cm-".

Column 4, lines 27-29 (Table 1):

Under column heading "Chemical Name", delete:

"2,2-
        di-
        oxide"

Replace with:

-- 2,2-di-oxide --

UNITED STATES PATENT AND TRADEMARK OFFICE
CERTIFICATE OF CORRECTION

PATENT NO. : 5,372,989

DATED : December 13, 1994

INVENTOR(S) : William L. Geigle et al

It is certified that error appears in the above-identified patent and that said Letters Patent is hereby corrected as shown below:

Column 5, line 2 (Table 1-continued):

Delete from left column heading "Cm-".

Column 6, line 2 (Table 1-continued):

Delete from left column heading "Cm-".

Column 7, line 2 (Table 1-continued):

Delete from left column heading "Cm-".

Signed and Sealed this

Thirty-first Day of October 1995

*Attest:*

BRUCE LEHMAN

*Attesting Officer*     *Commissioner of Patents and Trademarks*